US006767566B2

(12) United States Patent
Ausich et al.

(10) Patent No.: US 6,767,566 B2
(45) Date of Patent: Jul. 27, 2004

(54) METHOD OF ENHANCING THE EXTRACTION OF PROTEINASE INHIBITORS

(75) Inventors: Rod Ausich, Des Moines, IA (US); Hal Fallert, West Des Moines, IA (US); George Mather, Evergreen, CO (US); Brent Davieson, Ankeny, IA (US); Robert Stomp, Des Moines, IA (US); Fayad Z. Sheabar, West Des Moines, IA (US)

(73) Assignee: Kemin Consumer Care, L.C., Des Moines, IA (US)

( * ) Notice: Subject to any disclaimer, the term of this patent is extended or adjusted under 35 U.S.C. 154(b) by 0 days.

(21) Appl. No.: 09/900,555

(22) Filed: Jul. 6, 2001

(65) Prior Publication Data

US 2003/0092152 A1 May 15, 2003

(51) Int. Cl.$^7$ .............................................. A01N 65/00

(52) U.S. Cl. ...................... 424/773; 424/725; 426/425; 514/783

(58) Field of Search ............................. 424/773, 195.1, 424/725; 514/783; 930/250; 426/425

(56) References Cited

U.S. PATENT DOCUMENTS

| 4,491,578 A | | 1/1985 | Peikin |
| 4,906,457 A | | 3/1990 | Ryan |
| 5,187,154 A | | 2/1993 | Phillips et al. |
| 5,683,736 A | * | 11/1997 | Lunder ........................ 426/597 |
| 6,414,124 B1 | * | 7/2002 | Ryan et al. .................. 530/412 |

FOREIGN PATENT DOCUMENTS

WO          WO-9901474          1/1999

OTHER PUBLICATIONS

Ryan, C.A. and Walker–Simmons, M., "Plant Proteinase", In The Biochemistry of Plants, 1981, vol. 6, p. 321–350, Academic Press.
Melville, J.C. and Ryan, C.A., "Chymotrypsin inhibitor 1 from potatoes", J. Microb. Chem., 1972, 247: p. 3445–3453.
Plunkett, G. and Ryan, C.A., "Reduction and carboxamidomethylation of the single disulfide bond of proteinase inhibitor 1 from potato tubers. Effects on stability, immunological properties, and inhibitory activities", J. Biol. Chem., 1980, 255: 2752–2755.
Ryan, C.A., "Proteinase Inhibitors", In The Biochemistry of Plants, 1981, vol. 6, p. 351–370, Academic Press.
Campos, F.A.P. and Richardson, M., "The complete amino acid sequence of the bifunctional α–amylases/trypsin inhibitor from seeds of ragi (Indian finger millet; Eleusine coracana Goertn)", FEBS Lett., 1983, 152: 300–304.

Campos, F.A.P. and Richardson, M., "The complete amino acid sequence of α–amylases/trypsin inhibitor from seeds of ragi (Indian finger millet; Eleusine coracana Goertn)", FEBS Lett., 1984, 167: 221–225.
Ryan, C.A., "Purification and properties of a carboxypeptidase inhibitor from potatoes", J. Biol. Chem., 1974, 249: p. 5495–5499.
Bryant, J., Green, T.R., Gurusaddaiah, T., And Ryan, C.A., "Proteinase inhibitor II from potatoes: isolation and characterization of its protomer components", Biochemistry, 1976, 15: p. 3418–3424.
Beekwilder, J., Schipper, B., Bakker, P., Bosch, D., and Jongsma, M., "Characterization of potato proteinase inhibitor II reactive site mutants", Eur. J. Biochem., 2000, 267: p. 1975–1984.
Iwasaki, T., Kijohara, T., and Yoshikawa, J. Biol. Chem., 1972, 72: p. 1029, Tokyo.
Huang, C., MA, W.Y., Ryan, C.A., and Dong, Z., "Proteinase inhibitors I and II from potatoes specifically block UV–induced activator protein–1 activation through a pathway that is independent of extracellular signal regulated kinases, c–jun N–terminal kinases, and P38 kinase", Proc. Natl. Acad. Sci., 1997, 94: p. 11957–11962, U.S.
Hill, A.J., Peikin, S.R., Ryan, C.A., and Blundell, J.E., "Oral administration of proteinase inhibitor II from potatoes reduces energy intake in man", Physiol. Behav., 1990, 48: p. 241–246.
Schwartz, J.G., Guan, D., Green, G.M., and Phillips, W.T., "Treatment with an oral proteinase inhibitor slows gastric emptying and actually reduces glucose and insulin levels after a liquid meal in type II diabetic patients", Diabetes Cares, 1994, 17: p. 255–262.
Pearce, G. and Ryan, C.A., "A rapid, large–scale method for purification of metallo–carboxypeptidase from potato tubers", Anal. Biochem., 1983, 30: p. 223–225.

(List continued on next page.)

Primary Examiner—Jon Weber
Assistant Examiner—Patricia Patten
(74) Attorney, Agent, or Firm—Kent Herink; Daniel Rosenberg; Davis Law Firm

(57) ABSTRACT

The present invention provides a method for the extraction of a proteinase inhibitor from plant tissue. The extraction of the proteinase inhibitor begins with the addition of an alcohol-free, aqueous solution of an organic acid and a salt to plant tissue. The extraction solution and plant tissue are comminuted to reduce the average particle size of the plant tissue to improve extraction efficiencies. A weight ratio of between about 1:1 and about 1:10 extraction solution to plant tissue is used. In extracting proteinase inhibitor II from potato tubers, the extraction solution utilizes formic acid and sodium chloride, and the average particle size is reduced to between about 100 and 1500 microns. The process has been demonstrated to be cost-effective and provide high yields of the target proteinase inhibitor on commercial scales.

10 Claims, No Drawings

OTHER PUBLICATIONS

Armstrong, W.B., Kennedy, A.R., Wan, X.S., Atiba, J., McLaren, C.E., and Meyskens, F.L., Jr., "Single dose administration of Bowman–Birk inhibitor concentrate in patients with oral leukoplakia", *Cancer Epidemiol.,* 2000, 9: p. 43–47, Biomarkers Prev.

Billings, P.C., St. Clair, W.H., Maki, P.A., and Kennedy, A.R., "Distribution of the Bowman–Birk proteast inhibitor in mice following oral administrations", *Cancer Lett.,* 1992, 62: p. 191–197.

Duan, X., Li, X., Xue, Q., ABO–EL–SAAD, M., Xu, D., and Wu, R., "Transgenic rice plants harboring an introduced potato proteinase inhibitor II gene are insect resistant", *Nat. Biotechnol.,* 1996, 14: p. 494–498.

Hass, G.M., Hermodson, M.A., Ryan, C.A., and Gentry, L., "Primary structures of two low molecular weight proteinase inhibitors from potatoes", *Biochem.,* 1982, 16, 21, 752–756.

Keil, M., Sanchez–Serrano, J., Schell, J., and Willmitzer, L., "Primary structure of a proteinase inhibitor II gene from potato (*Solanum tuerosum*)", *Nuc. Acids Res.,* 1986, 14: p. 5841–5650.

Larionova, N.I., Balabushevich, N.G., Gladysheva, I.P., Moroz, N.A., Kazanskaia, N.F., Polekhina. O.V., and Donetskii, I.A., "Natural inhibitorsa as a basis for creating new drugs", *Vopr. Med. Khim,* 1994 40: p. 25–31.

Li, N., Qu, L.J., Liu, Y., Li, Q., Gu, H., and Chen Z., "The refolding, purification, and activity analysis of a rice Bowman–Birk inhibitor expressed in *Escherichia coli*", *Protein Expr. Purif.,* 1999, 15: p. 99–104.

Mitsumori, C., Yamagishi, K., Fujino, K., and Kikuta, Y., "Detection of immunologically related Kunitz and Bowman–Birk proteinase inhibitors expressed during potato tuber development", *Plant Mol. Biol.,* 1994, 26: p. 961–969.

Murray, C. and Christeller, J.T., "Genomic nucleotide sequence of a proteinase inhibitor II gene", *Plant Physiol.,* 1994, 106: p. 1681.

Otsuki, M., Tani, S., Fujii, M., Nakamura, T., Okabayashi, Y., and Koide, M., "Differential effects of protease inhibitor camostat on exocrine pancreas in fed and fasted rats", *Am. J. Physiol.,* 1993, 265 (Regulatory Integrative Com. Physiol. 34): R896–R901.

Pena–Cortex, H., Sanchez–Serrano, J., Prat. S., and Willmitzer, L., "Signals involved in the wound–induced expression of the proteinase inhibitor II gene of potato", Biochem. Soc. Symp., 1994, 60: p. 143–148.

Philips, W. and Schwartz, J.G., "Decelerating gastric emptying: therapeutic possibilities in type 2 diabetes", *Diabet. Med.,* 1996, 13: S44–48.

Pusztai, A., Grant, G., Bardocz, S., and Baintner, K., "Both free and complex trypsin inhibitors stimulate pancreatic secretion and change duodenal enzyme levels", *Am. J. Physiol.,* 1997, 272 (Gastrointest. Liver Physiol. 35): G340–G350.

Reddy, C.S., and Hayes, W.A., *Food Born Toxicants in Principles and methods of Toxicology,* 1994, p. 321–360, $3^{rd}$ ed., Edited by Hayes, A.W., Raven Press, New York, U.S.A.

Reeseland, J.E., Holm, H., Jacobsen, M.B., Jenssen, T.G., and Hanssen, L.E., "Proteinase inhibitors induce selective stimulation of human trypsin and chymotrypsin secretion", *J. Nutr.,* 1996, 126: p. 634–642.

Sanchez–Serano, J., Schmidt, R., Schell, J., and Willmitzer, L., "Nucleotide sequence of proteinase inhibitor encoding DNA of potato (*Solanum tuberosum*) and its mode of expression", *Mol. Gen. Genet.,* 1986, 203: p. 15–20.

Sang–Gon, Suh, Peterson, J.E., Steikema, W.J., and Hannapel, D.J., "Purification and characterization of the 22–kilodalton potato tuber proteins", *Plant Physiol.,* 1990, 94: p. 40–45.

Sugiyama, M., Atomi, Y., Wada, N., and Kuroda, A., Muto, "Effect of oral protease inhibitor administration on gallbladder motility in patients with mild chronic pancreatitis", *J. Gastroenterol.,* 1997, 32: p. 374–379.

\* cited by examiner

METHOD OF ENHANCING THE EXTRACTION OF PROTEINASE INHIBITORS

BACKGROUND OF THE INVENTION

1. Field of the Invention

The present invention relates to a method of enhancing the extraction of a proteinase inhibitor, and more specifically, to a method of improving the yield and purity of Proteinase Inhibitor-II (PI2) extracted from whole potatoes.

2. Background of the Prior Art

The extraction, isolation and purification of plant-derived proteins is well known in the field of biochemistry. In 1972, Melville and Ryan reported a large-scale preparation for isolating Chymotrypsin Inhibitor I from potato tubers (Melville, J. C. and Ryan, C. A. Chymotrypsin inhibitor I from potatoes. *J. Biological Chem.*, 247: 3445–3453, 1972). According to the method of Melville and Ryan, potatoes were sliced with peels intact and soaked in a sodium dithionite solution, homogenized, and expressed through nylon cloth. The resulting juice was adjusted to pH 3, centrifuged at 1000× g for 15 minutes at 5° F., and the supernatant collected and fractionated with ammonium sulfate.

Purification was achieved through water washing and heat treatment whereby clear filtrates of heated fractions were pooled and lyophilized. Suspending the lyophilized powder in water, dialyzing it against water for 48 hours, and lyophilizing the resulting clear filtrate obtained a crude extract. Resuspended extract was then centrifuged and applied to a column of Sephadex G-75. Collected fractions containing the Inhibitor I were pooled, evaporated, and desalted on a column of Sephadex G-25. The resulting gel-filtered inhibitor product was determined to be approximately 90% Inhibitor I protein purified by dissociation on a Sephadex G-75 column and desalted on a column of Sephadex G-25.

The Ryan lab followed-up by reporting the isolation and characterization of Proteinase Inhibitor II in much the same manner as described for Inhibitor I (Bryant, J., Green, T. R., Gurusaddaiah, T., Ryan, C. L. Proteinase inhibitor II from potatoes: Isolation and characterization of its protomer components. Biochemistry 15: 3418–3424, 1976). Bryant et al. differentiated potato-derived proteinase inhibitors into two groups based on their respective stabilities to a temperature of 80° C. for 10 minutes. Proteinase Inhibitor I ($PI_1$) is characterized as a tetrameric protein composed of four hybridized isoinhibitor protomer species having a molecular weight of 39,000, whereas $PI_2$ is characterized as a dimeric inhibitor comprising four isoinhibitor promoter species having a molecular weight of 21,000.

The extraction and isolation of proteinase inhibitor proteins from potatoes is described in WO 99/01474. Proteins from potato tubers are extracted in soluble form in an aqueous/alcohol extraction medium, such as dilute formic acid and 20% ethanol. The alcohol extract is heated to a first temperature to denature most of the unwanted proteins and cooled to a second temperature to form a precipitate phase constituting the debris and a soluble phase that contains the heat stable proteinase inhibitor proteins. The heat stable proteinase inhibitor proteins are precipitated from the soluble phase by dialysis against a suitable dialysis medium, such as dilute formic acid.

Recently, PI2 has been implicated in playing a role in extending satiety in subjects fed a nutritional drink composition containing PI2. U.S. patent application Ser. No. 09/624,922 describes that subjects reported a significant reduction in hunger for up to 3½ hours post meal when fed a meal comprising a nutritional drink composition containing PI2. Likewise, fullness ratings were enhanced, and each study subject lost an average of 2 kg over a 30-day period without experiencing the adverse side effects typically associated with appetite suppressing compounds. Mechanistically, it is thought that as a trypsin and chymotrypsin inhibitor, when consumed by a subject, PI2 stimulates the release of endogenous cholecystokinin, a known putative feedback agent effective in reducing the desire to intake food.

Existing methods for the extraction of proteinase inhibitors involve several laborious and time consuming steps and result in losses of yield and reduced purity of the recovered proteinase inhibitor. In addition, the most promising prior art methods rely on the use of ethanol in the extractant solution which, at the concentrations used, makes the solution flammable. None of the prior art processes have been demonstrated on a commercial scale. Accordingly, a need exists for a large-scale extraction process to extract PI2 in a cost-effective and efficient manner meeting industrial qualitative and quantitative standards.

SUMMARY OF THE INVENTION

Plant material containing a desired proteinase inhibitor is combined with a solution of an organic acid and a salt. The plant material is comminuted, forming a slurry in the acid and salt solution, to reduce the particle size and increase the surface area of the particles to improve the efficiency of the extraction. The process of comminution is selected to reduce the particle size without denaturing the desired proteinase inhibitor through local heating effects. The acid and salt solution enhances the extraction of the proteinase inhibitor from the comminuted plant material and protects it against degradation by other compounds that may be released from the ruptured plant cells. Once extracted into solution, the proteinase inhibitor is isolated and purified by centrifugation, clarification, filtration and drying of the extract solution. The acid and salt are removed during the filtration stage so as not to adulterate the purified proteinase inhibitor product.

In a preferred embodiment, proteinase inhibitor II (PI2) is extracted from whole potato tubers. Organic acids known to be effective in the process include acetic, ascorbic, citric and formic acid. Formic acid was found to result in the highest purity and highest yield of the final PI2 product. The formic acid content of the solution is adjusted in the range of 0.5% to 2.5% w/w, with a preferred content of approximately 1.5%. Sodium chloride is added to the extractant solution to increase the solubility of the potato proteins. Sodium chloride concentrations of between 1 N and 3 N are used. with a preferred concentration of approximately 1.5 N. The solution is added to the potatoes in a weight ratio of between 1:1 and 1:10, with a preferred ratio of 1:2.5 extraction solution:potato, w/w, respectively.

Comminution is accomplished by grinding. A target particle size is in the range of 100 to 1500 μm. In this range, product yields were increased and flow characteristics of the slurry were acceptable. Decreasing the particle size below 100 μm resulted in a lower recovery of PI2 and did not improve the flow characteristics. Grinding for an extended period of time also resulted in a reduced PI2 yield, most likely due to an increase in temperature and the release of undesired proteases that reduce the PI2 yield. The formic acid and sodium chloride are efficiently removed during the filtration stage.

An object of the present invention is to provide an improved method for the extraction of proteinase inhibitors from plant materials.

Another object of the invention is to provide an improved method for the extraction of proteinase inhibitor II from potato tubers which does not rely on the use of ethanol in the extraction solution.

A further object of the invention is to provide a method of extracting proteinase inhibitor II from potato tubers that is efficient and cost-effective on a commercial scale.

DETAILED DESCRIPTION OF THE INVENTION

The extraction and isolation of PI2 from potatoes begins with the addition of an organic acid, preferably formic acid, and a salt, preferably sodium chloride, to raw potatoes. The mixture is subjected to comminution to reduce the particle size of the potato particles and extract soluble proteins. Centrifugation is used to remove solids and the liquid fraction is heated at a temperature sufficient to denature many undesired proteins but not PI2. The solution is again centrifuged to remove the insoluble denatured proteins and the liquid fraction is microfiltered to remove relatively large particles. Ultrafiltration is used to remove the organic acid and salt and further purify the PI2 in the retentate.

A process for the extraction of PI2 from whole potatoes was developed in an attempt to maximize yield, minimize impurities, minimize cost, and achieve commercial feasibility. The extraction solution was evaluated based on the ability of the process to solubilize the $PI_2$, protect the PI2 from degradation, and maximize total PI2 removed from the insoluble potato components, while minimizing the amount of co-solubilized proteins. The extraction solution incorporated the solubility and functional stability of PI2 in acidic media and at elevated temperatures. An extraction solution containing sodium chloride and formic acid has been found effective for this purpose. The ratio of extraction solution utilized to raw material extracted was minimized for cost purposes, while producing the maximum yield of PI2 per kilogram of raw potato tubers.

Reverse Phase HPLC Method

The amount of PI2, Kunitz and carboxypeptidase inhibitors was measured using reverse phase HPLC. A Microsorb C-18 column (4.6 mm×250 mm, 5 μm particles with 300 Angstrom pore size; Varian Analytical Instruments) was used. Two mobile phase solvents were prepared, solvent A was 800 g deionized $H_2O$, 150 g acetonitrile, and 0.95 grams trifluoroacetic acid, and solvent B was 850 g acetonitrile and 0.85 g trifluoroacetic acid. Approximately 50 mg of the sample was added to 100 ml of solvent A. The sample was vortexed for 30 seconds, and then centrifuged at 10,000 rpm for 10 minutes. The supernatant was collected for RP-HPLC analysis. One hundred μl of the sample was injected into the column, with the pump set at 800–2500 psig, and a temperature of 30.0° C. The other flow rate, time, and solvent compositions are as set out in Table 1. The diode array of the detector was set at 220 nm.

TABLE 2

Protein Removal with Varying Sodium Chloride Levels

| [NaCl] N | Protein Eluting at 16–30 minutes mg/ml | Protein Eluting at ~23–30 minutes mg/ml | PI2 Level mg/ml |
|---|---|---|---|
| 0.0 | 0.504 | 0.378 | 0.167 |
| 0.1 | 0.298 | 0.184 | 0.160 |
| 0.2 | 0.245 | 0.141 | 0.172 |
| 0.3 | 0.178 | 0.076 | 0.149 |
| 0.4 | 0.150 | 0.071 | 0.169 |
| 0.5 | 0.119 | 0.076 | 0.189 |

An external standard was prepared to construct a standard curve for calibration of the column. Five mg of BSA were dissolved in 10 ml of solvent A. Four volumes, i.e., 25, 50, 75, and 100 μl, were injected into the column. A calibration curve was generated from the results.

EXAMPLE 1

Five hundred grams of potato tubers were extracted with 213 ml of 1% formic acid solution in a Waring blender for 2.5 minutes. The slurry was centrifuged at 10,000 rpm for 40 minutes. The liquid was decanted and filtered through #4 Whatman filter paper, yielding 486 g of clarified extract. Fifty grams of this clarified extract was poured into each of six 125 ml Erlenmeyer flasks equipped with magnetic stir bars. The amount of NaCl corresponding to Table 2 was added to each flack and stirred until the salt was dissolved. The flasks were then heated on high with stirring on a hot plate until the temperature of the extract reached 70° C. After ambient cooling to room temperature, the solutions were centrifuged at 12,000 rpm for 5 minutes and then analyzed using the above-described reverse phase HPLC method. The reported level of PI2 was calculated by integrating the area of the PI2 peak. The injection volume was 100 μl and the following equation was used to equate peak areas to protein levels:

$$\text{Protein (mg/ml)} = \left[\left(\frac{\text{peak area}}{4}\right) \times 8.17 \times 10^{-5}\right] + 0.0338$$

To clarified potato extract was added varying amounts of sodium chloride, followed by heating to 70° C. for 10 minutes. After cooling to room temperature, the solutions were analyzed for the protein eluting after PI2 in the HPLC method for PI2 quantification. The results are shown in Table 2.

TABLE 1

HPLC Conditions

| Time (min) | Flow rate (ml/min) | Solvent Composition (volume %) |
|---|---|---|
| 0 | 1 | 100% A |
| 5 | 1 | 100% A |
| 34 | 1 | 38% A |
| 38 | 1 | 100% B |
| 40 | 2 | 100% B |
| 45 | 2 | 100% B |
| 50 | 1 | 100% A |
| 55 | 1 | 100% A |

To establish the removal of Kunitz impurities from the potato extract, which have been shown to diminish the effectiveness of PI2 to increase satiety, the reverse phase HPLC method was used on a commercially available Kunitz standard purchased from SIGMA. A chromatograph of the Kunitz standard revealed that the major peak of the Kunitz impurities appears at approximately 25 minutes. Another inhibitor known to be present in potatoes is the carboxypeptidase inhibitor. The reverse phase HPLC method was used on a commercially available carboxypeptidase standard purchased from SIGMA. A chromatograph of the carboxypeptidase standard revealed that the major peaks of the carboxypeptidase impurities is a doublet that appears at approximately 17 minutes. At a level of 0.3 N sodium chloride and above, the post heat-treatment protein level remains relatively constant. The amount of PI2 remained relatively constant for all trials, indicating that at 70° C. no PI2 is precipitated at the salt levels up to 0.5 N. In order to reach the level of NaCl required in the heat-treatment phase, it is necessary to use an extractant with approximately 2 times the desired final salt concentration. Accordingly, a salt level of at least 0.3 N is desirable in the extraction solution during heat treatment at 70° C. to ensure efficient removal of Kunitz type proteins. Purity of the final PI2 product can be improved with greater amounts of sodium chloride.

EXAMPLE 2

An optimization study was performed to determine both the proper NaCl content and formic acid content of the extraction solution. The ideal extraction solution formulation would maximize the amount of PI2 liberated from the potato matrix, while minimizing the amount of protein contaminants solubilized. The liberation of PI2 was measured as yield, normalized to an extraction solution composition of 1.0 N NaCl. This was chosen as the normalization basis due to the previously stated prediction necessitating a two-fold increase of NaCl beyond the 0.5 N system shown effective for impurity removal in the heat-treatment stage. For optimization purposes, PI2 protein purity was measured and compared empirically to the normalized extraction yields. Extraction solutions containing NaCl concentrations from 0.0 N to 2.0 N were examined. In a similar manner, the formic acid content of the extraction solution was optimized. Formic acid contents ranging from 0.0 percent to 2.5 percent were studied.

TABLE 3

Sodium Chloride Optimization Data

| [NaCl] N | PI2 Area | Doublet Area | Time (min) | "Kunitz" Area | Time (min) |
|---|---|---|---|---|---|
| 0.0 | 4283.0 | 6402.2 | 17.28 | 83436.8 | ~23.5–29.0 |
| 1.0 | 6627.8 | 6294.6 | 17.28 | 131502.6 | ~23.5–29.0 |
| 1.0 | 4771.1 | 5571.2 | 16.97 | 113666.7 | ~23.5–29.0 |
| 2.0 | 5146.2 | 5306.3 | 16.95 | 120910.1 | ~23.5–29.0 |
| 0.0 | 4712.8 | 6231.8 | 17.48 | 83908.4 | ~23.5–29.0 |

TABLE 3-continued

Sodium Chloride Optimization Data

| [NaCl] N | PI2 Area | Doublet Area | Time (min) | "Kunitz" Area | Time (min) |
|---|---|---|---|---|---|
| 0.5 | 6592.7 | 6932.0 | 17.48 | 125256.4 | ~23.5–29.0 |
| 1.0 | 7578.4 | 7425.0 | 17.47 | 128660.5 | ~23.5–29.0 |
| 2.0 | 6822.6 | 6890.4 | 17.46 | 130632.2 | ~23.5–29.0 |
| 0.0 | 4235.2 | 6130.1 | 17.74 | 90357.4 | ~24.0–29.5 |
| 0.7 | 5964.6 | 6606.2 | 17.72 | 135932.2 | ~24.0–29.5 |
| 1.0 | 6746.7 | 6531.5 | 17.50 | 126617.3 | ~23.5–29.0 |
| 1.3 | 6062.5 | 6163.9 | 17.69 | 142488.8 | ~24.0–29.5 |
| 0.0 | 4699.6 | 6065.3 | 17.54 | 89125.2 | ~23.75–29.25 |
| 1.0 | 7768.5 | 6008.5 | 17.54 | 138907.2 | ~23.75–29.25 |
| 1.3 | 8095.2 | 6513.1 | 17.54 | 151858.8 | ~23.75–29.25 |
| 0.0 | 4743.7 | 5563.6 | 17.70 | 80937.5 | ~24.0–29.5 |
| 0.5 | 5825.3 | 5577.7 | 17.69 | 120352.4 | ~24.0–29.5 |
| 1.0 | 6848.1 | 5260.6 | 17.75 | 129407.5 | ~24.0–29.5 |
| 1.3 | 7173.2 | 5365.8 | 17.53 | 142758.6 | ~24.0–29.5 |

TABLE 4

Sodium Chloride Optimization Data Continued

| [NaCl] N | PI2 Area | PI2 (mg/ml) | Doublet Area | Protein (mg/ml) | "Kunitz" Area | Protein (mg/ml) |
|---|---|---|---|---|---|---|
| 0.0 | 4283.0 | 0.16 | 6402.2 | 0.20 | 83436.8 | 1.73 |
| 1.0 | 6627.8 | 0.21 | 6294.6 | 0.20 | 131502.6 | 2.68 |
| 1.0 | 4771.1 | 0.17 | 5571.2 | 0.19 | 113666.7 | 2.32 |
| 2.0 | 5146.2 | 0.18 | 5306.3 | 0.18 | 120910.1 | 2.47 |
| 0.0 | 4712.8 | 0.17 | 6231.8 | 0.20 | 83908.4 | 1.73 |
| 0.5 | 6592.7 | 0.21 | 6932.0 | 0.21 | 125256.4 | 2.55 |
| 1.0 | 7578.4 | 0.23 | 7425.0 | 0.22 | 128660.5 | 2.62 |
| 2.0 | 6822.6 | 0.21 | 6890.4 | 0.21 | 130632.2 | 2.66 |
| 0.0 | 4235.2 | 0.16 | 6130.1 | 0.20 | 90357.4 | 1.86 |
| 0.7 | 5964.6 | 0.19 | 6606.2 | 0.21 | 135932.2 | 2.76 |
| 1.0 | 6746.7 | 0.21 | 6531.5 | 0.20 | 126617.3 | 2.58 |
| 1.3 | 6062.5 | 0.20 | 6163.9 | 0.20 | 142488.8 | 2.89 |
| 0.0 | 4699.6 | 0.17 | 6065.3 | 0.20 | 89125.2 | 1.84 |
| 1.0 | 7768.5 | 0.23 | 6008.5 | 0.19 | 138907.2 | 2.82 |
| 1.3 | 8095.2 | 0.24 | 6513.1 | 0.20 | 151858.8 | 3.08 |
| 0.0 | 4743.7 | 0.17 | 5563.6 | 0.19 | 80937.5 | 1.68 |
| 0.5 | 5825.3 | 0.19 | 5577.7 | 0.19 | 120352.4 | 2.46 |
| 1.0 | 6848.1 | 0.21 | 5260.6 | 0.18 | 129407.5 | 2.63 |
| 1.3 | 7173.2 | 0.22 | 5365.8 | 0.18 | 142758.6 | 2.90 |

TABLE 5

Sodium Chloride Optimization Data Continued

| [NaCl] N | PI2 (mg/ml) | PI2 mg | Normalized yield | Doublet (mg/ml) | Doublet (mg) | Kunitz (mg/ml) | Total Kunitz (mg) | Purity |
|---|---|---|---|---|---|---|---|---|
| 0.0 | 0.16 | 78.25 | 77.51% | 0.20 | 98.76 | 1.73 | 844.50 | 7.66% |
| 1.0 | 0.21 | 100.75 | 100.00% | 0.20 | 97.53 | 2.68 | 1307.21 | 6.69% |
| 1.0 | 0.17 | 79.59 | 100.00% | 0.19 | 87.02 | 2.32 | 1090.74 | 6.33% |
| 2.0 | 0.18 | 82.23 | 104.38% | 0.18 | 83.70 | 2.47 | 1146.21 | 6.27% |
| 0.0 | 0.17 | 81.88 | 74.82% | 0.20 | 96.49 | 1.73 | 843.57 | 8.01% |
| 0.5 | 0.21 | 100.78 | 91.34% | 0.21 | 104.07 | 2.55 | 1251.43 | 6.92% |

TABLE 5-continued

Sodium Chloride Optimization Data Continued

| [NaCl] N | PI2 (mg/ml) | PI2 mg | Normalized yield | Doublet (mg/ml) | Doublet (mg) | Kunitz (mg/ml) | Total Kunitz (mg) | Purity |
|---|---|---|---|---|---|---|---|---|
| 1.0 | 0.23 | 104.63 | 100.00% | 0.22 | 103.22 | 2.62 | 1218.05 | 7.34% |
| 2.0 | 0.21 | 97.11 | 93.36% | 0.21 | 97.73 | 2.66 | 1228.97 | 6.82% |
| 0.0 | 0.16 | 72.99 | 82.29% | 0.20 | 90.21 | 1.86 | 855.33 | 7.17% |
| 0.7 | 0.19 | 88.27 | 92.58% | 0.21 | 94.07 | 2.76 | 1263.08 | 6.11% |
| 1.0 | 0.21 | 100.78 | 100.00% | 0.20 | 98.72 | 2.58 | 1246.21 | 6.97% |
| 1.3 | 0.20 | 93.49 | 93.51% | 0.20 | 94.45 | 2.89 | 1386.67 | 5.94% |
| 0.0 | 0.17 | 80.77 | 73.47% | 0.20 | 93.75 | 1.84 | 883.03 | 7.64% |
| 1.0 | 0.23 | 111.08 | 100.00% | 0.19 | 94.18 | 2.82 | 1370.31 | 7.05% |
| 1.3 | 0.24 | 113.59 | 102.82% | 0.20 | 98.48 | 3.08 | 1486.42 | 6.69% |
| 0.0 | 0.17 | 80.41 | 80.24% | 0.19 | 88.13 | 1.68 | 797.53 | 8.32% |
| 0.5 | 0.19 | 92.04 | 90.39% | 0.19 | 89.68 | 2.46 | 1187.23 | 6.72% |
| 1.0 | 0.21 | 100.96 | 100.00% | 0.18 | 85.91 | 2.63 | 1263.04 | 6.96% |
| 1.3 | 0.22 | 99.55 | 103.05% | 0.18 | 83.15 | 2.90 | 1329.54 | 6.58% |

TABLE 6

Average Normalized Yields and Purities With Varying NaCl

| NaCl Normality | Average Yield | Average Purity |
|---|---|---|
| 0.0 | 77.67% | 7.76% |
| 0.5 | 90.87% | 6.82% |
| 0.7 | 92.58% | 6.11% |
| 1.0 | 100.00% | 6.89% |
| 1.3 | 99.80% | 6.40% |
| 2.0 | 98.87% | 6.54% |

While NaCl normalities of 0.5 N and above were seen to give high yields, a normality of 1.0 N was selected as maximizing both yield and purity.

TABLE 7

Formic Acid Optimization Data

| Formic acid conc. | PI2 Area | Impurity Peak Area | Time (min) | Doublet Area | Time (min) | "Kunitz" Area | Time (min) |
|---|---|---|---|---|---|---|---|
| 0.0% | 7483.6 | 2453.50 | 15.63 | 6848.6 | 17.56 | 225054.1 | ~23.75–31.0 |
| 1.5% | 7768.5 | 797.67 | 15.73 | 6008.5 | 17.54 | 138907.2 | ~23.75–29.25 |
| 0.1% | 8252.0 | 2867.90 | 15.59 | 7071.5 | 17.54 | 226680.4 | ~23.75–30.5 |
| 0.5% | 7165.9 | 2071.70 | 15.65 | 6198.6 | 17.53 | 203839.7 | ~23.75–30.5 |
| 1.0% | 8353.7 | 813.80 | 15.61 | 5873.0 | 17.50 | 161433.2 | ~23.75–29.25 |
| 1.5% | 7939.3 | 893.50 | 15.64 | 5979.0 | 17.54 | 135420.3 | ~23.75–29.25 |
| 0.1% | 7005.0 | 1805.90 | 14.85 | 7788.5 | 17.00 | 233105.7 | ~23.75–30.0 |
| 1.5% | 7407.2 | 962.20 | 15.10 | 6109.7 | 16.98 | 144764.2 | ~23.5–29.0 |
| 2.0% | 7116.2 | 1117.55 | 15.11 | 6441.2 | 16.97 | 187670.8 | ~23.25–30.0 |
| 2.5% | 7318.8 | 1176.40 | 15.07 | 6649.6 | 16.97 | 180476.2 | ~23.25–30.0 |

TABLE 8

Formic Acid Optimization Data

| Formic acid conc. | PI2 Area | PI2 (mg/ml) | Impurity Peak Area | Protein (mg/ml) | Doublet Area | Protein (mg/ml) | "Kunitz" Area | Protein (mg/ml) |
|---|---|---|---|---|---|---|---|---|
| 0.0% | 7483.6 | 0.19 | 2453.50 | 0.09 | 6848.6 | 0.17 | 225054.1 | 4.37 |
| 1.5% | 7768.5 | 0.23 | 797.67 | 0.09 | 6008.5 | 0.19 | 138907.2 | 2.82 |
| 0.1% | 8252.0 | 0.20 | 2867.90 | 0.10 | 7071.5 | 0.18 | 226680.4 | 4.40 |
| 0.5% | 7165.9 | 0.18 | 2071.70 | 0.08 | 6198.6 | 0.16 | 203839.7 | 3.96 |
| 1.0% | 8353.7 | 0.20 | 813.80 | 0.06 | 5873.0 | 0.16 | 161433.2 | 3.15 |
| 1.5% | 7939.3 | 0.19 | 893.50 | 0.06 | 5979.0 | 0.16 | 135420.3 | 2.65 |
| 0.1% | 7005.0 | 0.18 | 1805.90 | 0.08 | 7788.5 | 0.19 | 233105.7 | 4.53 |
| 1.5% | 7407.2 | 0.18 | 962.20 | 0.06 | 6109.7 | 0.16 | 144764.2 | 2.83 |
| 2.0% | 7116.2 | 0.18 | 1117.55 | 0.06 | 6441.2 | 0.17 | 187670.8 | 3.65 |
| 2.5% | 7318.8 | 0.18 | 1176.40 | 0.06 | 6649.6 | 0.17 | 180476.2 | 3.52 |

TABLE 9

Formic Acid Optimization Data

| Formic acid conc. | PI2 (mg/ml) | PI2 mg | Imp. (mg/ml) | Impurity mg | Doublet (mg/ml) | Doublet mg | "Kunitz" (mg/ml) | "Kunitz" mg | Yield | Purity |
|---|---|---|---|---|---|---|---|---|---|---|
| 0.0% | 0.19 | 88.80 | 0.09 | 42.64 | 0.17 | 82.97 | 4.37 | 2085.22 | 79.93% | 3.86% |
| 1.5% | 0.23 | 111.08 | 0.09 | 44.15 | 0.19 | 94.18 | 2.82 | 1370.31 | 100.00% | 6.86% |
| 0.1% | 0.20 | 98.57 | 0.10 | 47.76 | 0.18 | 87.43 | 4.40 | 2159.78 | 104.57% | 4.12% |
| 0.5% | 0.18 | 85.43 | 0.08 | 38.93 | 0.16 | 76.60 | 3.96 | 1880.60 | 90.63% | 4.10% |
| 1.0% | 0.20 | 94.56 | 0.06 | 28.10 | 0.16 | 75.38 | 3.15 | 1529.05 | 100.56% | 5.69% |
| 1.5% | 0.19 | 94.26 | 0.06 | 28.71 | 0.16 | 76.02 | 2.65 | 1280.14 | 100.00% | 6.37% |
| 0.1% | 0.18 | 88.79 | 0.08 | 38.60 | 0.19 | 96.35 | 4.53 | 2271.21 | 96.55% | 3.56% |
| 1.5% | 0.18 | 91.96 | 0.06 | 30.23 | 0.16 | 79.53 | 2.83 | 1407.70 | 100.00% | 5.71% |
| 2.0% | 0.18 | 88.75 | 0.06 | 31.56 | 0.17 | 82.31 | 3.65 | 1809.93 | 96.50% | 4.41% |
| 2.5% | 0.18 | 88.56 | 0.06 | 31.37 | 0.17 | 82.33 | 3.52 | 1700.64 | 96.30% | 4.65% |

TABLE 10

Average Normalized Yields and Purities With Varying Formic Acid

| % Formic acid | Average yield | Average purity |
|---|---|---|
| 0.0 | 79.93% | 3.86% |
| 0.1 | 100.56% | 3.84% |
| 0.5 | 90.63% | 4.10% |
| 1.0 | 100.56% | 5.69% |
| 1.5 | 100.00% | 6.31% |
| 2.0 | 96.50% | 4.41% |
| 2.5 | 96.30% | 4.65% |

The data indicate the use of 1.5% formic acid content for the extraction solution. While other formic acid concentrations offer similar yield, 1.5% formic acid content clearly maximizes purity.

EXAMPLE 3

An experiment was conducted to determine the effect on yield by using varying amounts of the extraction solution comprised of 1.5% formic acid and 1.0 N NaCl in water. The weight ratio of potatoes to extraction solution was varied from 1:1 to 1:10. The ratios used and the observed yields are reported in Table 11.

TABLE 11

Average Normalized PI2 Yield and Liquid Yield With Varying Extraction Ratio

| Extraction ratio | Normalized, Average Yield | Average Yield in mg/kg |
|---|---|---|
| 0.1 | 22.38% | 24.07 |
| 0.2 | 60.47% | 64.94 |
| 0.3 | 85.56% | 91.98 |
| 0.4 | 100.00% | 107.32 |
| 0.5 | 100.42% | 107.76 |
| 0.6 | 101.03% | 108.49 |
| 0.7 | 100.42% | 107.74 |
| 0.8 | 100.74% | 108.09 |
| 0.9 | 101.21% | 108.57 |
| 1.0 | 101.38% | 108.81 |

While the highest yield is achieved with the highest ratio of extraction solution, the gain in total yield is minimal above the 0.4 to one ratio (1:2.5 w/w extraction solution to potatoes, respectively). This ratio has been selected, in order to minimize extraction solution cost and material handling concerns, such as heating, cooling and evaporation.

The data dictate the choice of approximately 1.0 N sodium chloride as the preferred concentration in the extraction solution for the isolation of PI2. Using 1.0 N sodium chloride results in maximized yield of PI2 under the tested conditions, and although other concentrations are capable of producing similar yields, the PI2 protein purity that is represented by the use of 1.0 N NaCl is maximized at 1.0 N. Higher PI2 protein purity could be achieved by using less sodium chloride, however this would result in a reduced PI2 yield. This level of sodium chloride is also appropriate for the removal of the Kunitz type impurities. Similarly, the data dictate the selection of 1.5% formic acid as the preferred concentration for the extraction of PI2. An extraction solution that contains 1.5% formic acid exhibits beneficial antimicrobial and anti-proteolytic behavior. The yield of PI2 is maximized under the tested conditions at 1.5% formic acid content in the extraction solution, and this concentration also provides the highest PI2/Kunitz purity of the formulations that attain comparable yields. There is no significant increase in total yield when creating a slurry that is composed of greater than thirty percent extraction solution by weight. A slurry of thirty percent extraction solution composition is roughly equivalent to a one-part extraction solution to two and one-half parts raw material (1:2.5 solvent:solid ratio).

EXAMPLE 4

A liquid extraction solution containing approximately 1.0 N sodium chloride and 1.5% formic acid was found to be solubilizing PI2 while retaining its functional stability. The extraction system was examined to optimize the release of the target protein from the potato cellular matrix. physical grinding is necessary to rupture the potato tuber cells and thereby release the protein into the liquid phase. The final grind profile of the potato slurry was examined for complete release of soluble proteins into liquid phase, minimal PI2 degradation, and ease of liquid/solid separation. Grind profile and extraction efficiency correlations were examined, followed by separation ease of the optimized grind profile.

A set of stackable sieves conforming to ASTM specification 11 is assembled with the largest sieve size on top and the rest placed in descending sieve size. The sieve size range should be chosen so as to capture at least 95% of the solids in the suspension to be sized. Approximately 250 grams of the suspension to be sized is poured onto the top of the sieve stack. The top sieve is washed repeatedly with water until no more solids appear to be passing through the sieve. This sieve is then removed and this washing repeated for each sieve. The contents of each sieve are placed in pre-weighed weigh boats and placed in a vacuum oven at less than 100° C., but more than 50° C., to dry for at least 12 hours. After the solids are dry their weights are measured on an analytical balance and recorded. The particle size distribution is reported as the dry weight of the solids retained on each sieve expressed as a percentage of total dry solids retained. Results are reported in Table 12 using micrometers as the size unit.

TABLE 12

Sample Size Distribution Report

| Particle Size μ (micrometers) | % Solids Retained |
|---|---|
| 1170 | 11 |
| 1080 | 32 |
| 625 | 38 |
| 400 | 19 |

For these trails whole, raw potatoes were extracted using an aqueous solution of 1.5% formic acid and 1.0 N NaCl in a weight ratio 1:2.5 extraction solution to potatoes. PI2 concentration was derived sing reverse phase HPLC method described previously.

The degree of disintegration of the potato in the presence of the extraction solution has been studied. To test this aspect of the extraction, samples of the optimized extraction solution and whole, raw potatoes were ground using commercially available Commitrol grinders. The test protocol was designed to determine the grinding device's ability to generate to a number of consistent target profiles, and examine the particle size distribution within these grinds. The experimentally ground slurries were analyzed for PI2 content. A trend was discovered in which a finer grind profile exhibited increased yield of PI2 on a mg/kg basis. Extractions with an average particle size of greater than 1000 μm showed a marked diminution of PI2 extraction efficacy.

When ground on a Urschel grinder to a nominal particle size of less than 100 μm, the samples yielded 85 mg PI2 per kg of potato. A similar test done using the same lot of potatoes and extractive solution using a Hobart grinder giving a grind size of approximately 1500 μm afforded 70 mg PI2 per kg of potato.

TABLE 13

Comparison of Coarse and Fine Grind Processes

| Grinder | Potatoes (kg) | Extraction solution | Average particle size-μm (micrometers) | Total slurry (kg) | PI2 mg/kg potato |
|---|---|---|---|---|---|
| Hobart Coarse | 5.59 | 2.24 | ~1500 | 7.83 | 70 |
| Urschel Fine | 5.72 | 2.29 | <90 | 11.03 | 85 |

There was not an appreciable difference of ease of filtration under the conditions adopted for this experiment. The final pulp recovered from the Urschel grind was 17.3% by weight of the slurry and contained a moisture level of 49.8%. The pulp recovered from the Hobart grind was 31.9% by weight of the slurry and contained a moisture level of 60.5%. This represents a potential loss in yield of approximately 10 percent in the more coarse grind profile, using a liquid yield weight percentage (7.1% residual liquid in the finely ground waste solids as opposed to 17.2% residual liquid in the coarsely ground waste solids).

In addition to PI2 and mass balance losses, the finer grind does exhibit a greater amount of total protein extracted using the finer grind protocol. The resulting liquid extracts were assayed using the reverse phase HPLC method. The fine grind extract does contain a greater concentration of undesirable proteins. In particular, the PI2/Kunitz purity (taken as the concentration of PI2 divided by the total concentration of the Kunitz impurities and the PI2) decreases from 7.41 percent purity for the coarse grind and 5.99 percent purity in the extract resulting from the fine grind.

A further study examined the yield of P12 using a variety of grind profiles. The grind profiles examined varied from 300 μm average particle size to 1200 μm average size.

TABLE 14

Optimization of Grinding Profile and PI2 Yield

| Average grind profile | Gap | PI2 yield | Kunitz content | PI2/ 'Kunitz' purity | Temperature increase |
|---|---|---|---|---|---|
| Approx. 300 micron | 214 μ | 98.55% | 105.77% | 48.23% | 13.1° C. |
| Approx. 500 micron | 388 μ | 100.00% | 100.00% | 50.00% | 10.4° C. |
| Approx. 700 micron | 633 μ | 93.68% | 97.94% | 48.89% | 8.8° C. |
| Approx. 900 micron | 968 μ | 91.32% | 94.88% | 49.05% | 6.7° C. |
| Approx. 1200 micron | 1519 μ | 86.57% | 84.97% | 50.47% | 5.2° C. |

Table 14 presents the optimization study for final grind profile with respect to PI2 yield. The yields and purities are normalized to the highest PI2 yield in the sample set. The highest yield was observed at approximately 500 μm average particle size. The PI2/Kunitz purity is also acceptable, only one other grind profile exhibited a higher purity, however with an unacceptable sacrifice in PI2 yield. In order to produce the desired grind profile at the pilot scale, a "Microcut Head Assembly" was used. The final grind profile is determined by several mechanical characteristics of the grinding head, such as the number, spacing and angle of blades in the head as well as the speed and type of impeller. The Microcut head features 190 tungsten carbide blades, each 0.084 inches thick. This thickness allows for a spacing of 0.0153 inches (388.62 μ) between each blade. The product is pushed through the spaces between the blades by the impeller. The impeller being used is a "veri-cut" due to its durability and the uniform particle size it produces. This impeller, in conjunction with this head assembly, produces a depth of cut of 0.0016 inches (40.64 μ). The interaction of the impeller, grinding blades and raw materials generates the friction responsible for the observed temperature rise. A rise of ten degrees was not considered harmful, due to the heat stability of PI2 (70° C. for more than 3 hours). The depth of cut may vary slightly with the speed of the impeller, which is determined by the motor. For these studies, a consistent grind profile was used to provide an average particle size of approximately 500 μm.

Trials were then conducted, using the optimized grind profile, to determine the proper separation conditions of the liquid/solid slurry. There are many techniques available to separate solids from liquids. A basket type centrifuge was identified as appropriate for the separation of potato solids from the extraction solution mixture. The target goals for the separation process were to maximize the liquid extracted from the slurry, while generating a cake with a minimized moisture content. As the PI2 is expected to disperse within the liquid fraction, maximizing liquid recovery is of primary importance to maximizing the yield of PI2. Pilot trials were performed, using a pilot model that would be directly scaleable to a full production model. The characteristic of the centrifuge that was optimized by these trials was the filter-mesh screen size.

TABLE 15

Screen Mesh Trial for Optimization

| Mesh size | Liquid recovery | Solid moisture content | Suspended solid | Time per L collected |
|---|---|---|---|---|
| 100 μ | 100.00% | 5.35% | 5.35% | 0.972 L/min |
| 75 μ | 99.87% | 5.78% | 4.55% | 0.968 L/min |
| 50 μ | 99.54% | 5.94% | 1.05% | 0.967 L/min |
| 35 μ | 99.13% | 6.05% | 0.25% | 0.960 L/min |
| 15 μ | 98.65% | 6.74% | 0.15% | 0.933 L/min |

The liquid recovery data was normalized to the highest yield examined over the data set, the moisture content if the solid cake was measured via vacuum oven digestion, and the suspended solids were determined via gyro-testing. Based on the data from Table 15, a 35 μ filter bag mesh was chosen for continued pilot study, and for full production. The liquid yield is maximized (over the sample set tested) utilizing the largest screen mesh. Unfortunately, this screen mesh also generates the highest amount of suspended solid in the filtered extract. It can be observed that a dramatic reduction in the amount of suspended solid is observed using filter bags below 75μ. The reduction of suspended solids achieved using a 35 μ filter, combined with the acceptable yield and collection rate, made the 35 μ bag the preferred choice.

The foregoing description comprise illustrative embodiments of the present inventions. The foregoing embodiments and the methods described herein may vary based on the ability, experience, and preference of those skilled in the art. Merely listing the steps of the method in a certain order does not necessarily constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

What is claimed is:

1. A method for extraction of a proteinase inhibitor from raw potato tubers comprising the steps of:
   (a) preparing an alcohol-free extraction solution by adding to water, an organic acid in an amount to provide a concentration between about 0.5 weight percent and about 2.5 weight percent, and adding a salt to the water in an amount to provide between about 0.3 and 2.0 normality with regard to the salt;
   (b) adding the raw potato tubers to the extraction solution in a weight ratio of between about 1:1 and about 1:10 extraction solution of raw potato tubers;
   (c) comminuting the raw potato tubers in the extraction solution to reduce the mean particle size of the plant material to between about 100 microns and about 1500 microns thereby creating a slurry containing a liquid and a solid fraction; and
   (d) recovering said liquid fraction from said slurry to obtain a proteinase inhibitor.

2. The method of claim 1 wherein the organic acid is selected from the group consisting of acetic, ascorbic, citric, and formic acid.

3. The method of claim 2 wherein the organic acid is formic acid and the salt is sodium chloride.

4. The method of claim 3 wherein the formic acid concentration is between about 1.2 and 1.7 weight percent, and the sodium chloride normality is between about 0.8 and 1.5.

5. The method of claim 1 further comprising the step of filtering the slurry to remove a portion of the particles leaving a clarified liquid extract which contains the extracted proteinase inhibitor.

6. The method of claim 1 wherein the weight ratio of extraction solution to raw potato tubers is between about 1:1.5 and 1:4.

7. The method of claim 6 wherein the weight ratio of extraction solution to potato tubers is between about 1:2 and 1:3.

8. The method of claim 1 wherein the resulting average particle size of the tuber in the mixture is less than about 1000 μm.

9. The method of claim 8 further comprising the step of filtering the slurry to remove a portion of the particles leaving a clarified liquid extract which contains the extracted proteinase inhibitor, and wherein the resulting average particle size is less than about 1000 μm and the filtering step uses a filter having a screen size of between about 15 μm and about 100 μm.

10. The method of claim 1 wherein the comminuting step does not raise the temperature of the slurry above 90° C.

* * * * *

UNITED STATES PATENT AND TRADEMARK OFFICE
CERTIFICATE OF CORRECTION

PATENT NO. : 6,767,566 B2  
DATED : July 27, 2004  
INVENTOR(S) : Ausich et al.

It is certified that error appears in the above-identified patent and that said Letters Patent is hereby corrected as shown below:

<u>Title page,</u>
Item [75], Inventor, should read:
-- Brent Davison
Ankeny, Iowa (US) --

Signed and Sealed this

Fifteenth Day of February, 2005

JON W. DUDAS
*Director of the United States Patent and Trademark Office*